(12) United States Patent
Kelley

(10) Patent No.: US 9,757,135 B1
(45) Date of Patent: Sep. 12, 2017

(54) TREPHINE REAMER FOR USE IN REMOVAL OF A FEMORAL COMPONENT OF A HIP REPLACEMENT IMPLANT

(71) Applicant: Scott Kelley, Chapel Hill, NC (US)

(72) Inventor: Scott Kelley, Chapel Hill, NC (US)

( * ) Notice: Subject to any disclaimer, the term of this patent is extended or adjusted under 35 U.S.C. 154(b) by 473 days.

(21) Appl. No.: 14/303,899

(22) Filed: Jun. 13, 2014

Related U.S. Application Data

(60) Provisional application No. 61/835,088, filed on Jun. 14, 2013.

(51) Int. Cl.
*A61B 17/00* (2006.01)
*A61B 17/16* (2006.01)

(52) U.S. Cl.
CPC ...... *A61B 17/1668* (2013.01); *A61B 17/1637* (2013.01)

(58) Field of Classification Search
CPC .................. A61B 17/1668; A61B 17/1637
USPC ...................................... 606/79–85
See application file for complete search history.

(56) References Cited

U.S. PATENT DOCUMENTS

| | | | |
|---|---|---|---|
| 5,382,251 A | 1/1995 | Hood et al. | |
| 5,954,671 A * | 9/1999 | O'Neill | A61B 17/1637 600/567 |
| 6,187,012 B1 | 2/2001 | Masini | |
| 7,004,972 B2 | 2/2006 | Yoon | |
| 8,414,585 B2 | 4/2013 | Meneghini et al. | |
| 2004/0236341 A1 | 11/2004 | Petersen | |
| 2005/0090830 A1 | 4/2005 | Salazar et al. | |
| 2007/0270711 A1* | 11/2007 | Gil | A61B 10/025 600/567 |
| 2011/0046745 A1 | 2/2011 | Daniels et al. | |
| 2011/0112540 A1 | 5/2011 | McLean et al. | |
| 2011/0160732 A1* | 6/2011 | Liao | A61B 17/1637 606/80 |
| 2012/0184964 A1 | 7/2012 | Hudak, Jr. et al. | |

OTHER PUBLICATIONS

Callaghan et al., ed. The Adult Hip. vol. 2, 2nd ed. Chapter 60, pp. 884-910, and Chapter 70, pp. 1025-1035. 2007. Lippincott Williams & Wilkins, Philadephia, PA.
Hansen et al. "The Rottinger approach for total hip arthroplasty: technique and review of the literature" Curr Rev. Musculoskelet Med (2011) 4:132-138. Springer, Berlin, Germany.
"Zimmer Natural-Hip™ System Surgical Technique" Informational Booklet. 25 pages. 2005. Zimmer, Inc. Warsaw, IN.

(Continued)

*Primary Examiner* — Matthew Lawson
(74) *Attorney, Agent, or Firm* — Coats & Bennett, PLLC

(57) ABSTRACT

Trephine reamers that include a body with a hollow interior sized to receive a femoral component. A distal end of the body includes one or more teeth shaped for cutting the femur. Valleys are positioned between the teeth. The valleys accommodate the cut bone and prevent and/or reduce interference with the cutting teeth. Thus, a single trephine reamer is able to cut a greater amount of bone. Methods of cutting the femur including positioning the trephine reamer over the femoral component, and rotating the reamer such that the teeth cut the bone that extends around the component. The reamer moves along the length of the component during the cutting thus allowing for removal of the component.

14 Claims, 8 Drawing Sheets

(56) References Cited

OTHER PUBLICATIONS

"CPT® 12/14 Hip System. Surgical Technique for Primary Hip Arthroplasty" Informational Booklet. 27 pages. 2002. Zimmer, Inc. Warsaw, IN.
"Alloclassic® Hip System Surgical Technique" Informational Booklet. 20 pages. 2003. Zimmer, Inc. Warsaw, IN.
"ZMR® Hip System" Informational literature, 20 pages. 2003. Zimmer, Inc. Warsaw, IN.
"Zimmer® M/L Taper Hip Prosthesis. Surgical Technique" Informational Booklet. 16 pages. 2010. Zimmer, Inc. Warsaw, IN.
"SYNERGY Cemented Stem Surgical Technique" Informational Booklet, 31 pages. 2004. Smith & Nephew, Inc., Memphis. TN.
"SYNERGY Cementless Stem Surgical Technique" Informational Booklet, 32 pages. 2004. Smith & Nephew, Inc., Memphis, TN.
"ZMR Revision Taper Hip Prosthesis, Surgical Technique for Revision Hip Arthroplasty" 26 pages. 1999. Zimmer, Inc. Warsaw, IN.
"Summit® titanium tapered stem." Product description and illustration, 1 page. 2001. DePuy Orthopaedics, Inc., Warsaw, IN.
Morrey, Bernard, ed. Joint Replacement Arthroplasty. Chapter 44, pp. 619-638. 1991. Churchill Livingstone, Inc., New York, NY.
"Cheng Biopsy Trephine System." Product data sheet. Viewed online Jun. 10, 2014, at http://www.innomed.net/PDFsinnomed/InnoChengBiopsyTrephineSystem.pdf. Innomed, Inc. Savannah, GA.
Vasireddy, A., et al., "Use of a Trephine to Extract Broken Femoral Stems." Ann R Coll Surg Engl, Nov. 2008; 90(8): 699-740. Royal College of Surgeons of England, London, UK.
Kancherla, V.K., et al., "Utility of Trephine Reamers in Revision Hip Arthroplasty." The Journal of Arthroplasty 29 (1), Jan. 2014. pp. 210-213. Elsevier, Amsterdam, NL.
"DePuy Revision Solutions. Hip Extraction Instrumentation Product Overview." 16 pages. 2009. DePuy Orthopaedics, Inc, Warsaw, IN.
Tanaka, T., et al., "A new strategy to remove broken femoral mega-prostheses with hollow trephine reamers." Eur J Orthop Sur Traumatol (2013) 23:357-360. Springer-Verlag, Berlin, Germany.
"Moreland Cementless Hip Revision instrumentation." Product Overview. 12 pages. 2008. DePuy Orthopaedics, Inc. Warsaw, IN.
"Hip Labial Disorders." Conolty, Karolyn, ed., et al. Physiopedia. Accessed Aug. 28, 2414, at http://www.physio-pedia.com/Hip_Labral_Tears.

\* cited by examiner

TREPHINE REAMER FOR USE IN REMOVAL OF A FEMORAL COMPONENT OF A HIP REPLACEMENT IMPLANT

CROSS-REFERENCE TO RELATED APPLICATIONS

The present application claims the benefit of U.S. Application No. 61/835,088 filed on Jun. 14, 2013, and entitled Trephine Reamer for Use in Removal of a Femoral Component of a Hip Replacement Implant. This application is hereby incorporated by reference in its entirety.

FIELD OF THE INVENTION

The present application is directed to a hollow trephine reamer for use in cutting the femur for removing a portion or entirety of a femoral component of a hip replacement implant.

BACKGROUND

Hip replacement procedures involve the replacement of the hip joint formed by the head of the femur and the acetabulum of the pelvic bone. Hip replacement procedures include the preparation of the femur for receipt of a femoral component and preparation of the acetabulum to receive an acetabulum component. The two components engage together to replace the hip joint.

FIG. 1 illustrates a hip replacement implant 100 positioned within a patient. The implant 100 includes the femoral component 101 that is attached to the femur 110, and an acetabular component 102 that is attached to the acetabulum 111 in the pelvic bone 112. The femoral component 101 includes a head 103 that seats within a receptacle of the acetabular component 102. This replacement joint replicates the hip joint and provides for pivoting movement of the femur 110 relative to the pelvic bone 112.

The femoral component 11 is implanted into the femoral canal of the femur 100. After implantation, bone growth occurs with the femoral component to secure its position within the femur 110.

In some instances, it is necessary to remove the femoral component 101 from the femur 110 during a revision procedure after implantation and bone growth. FIG. 2A illustrates one situation in which the femoral component 101 is fractured into two sections while implanted in the femur 110. FIG. 2B illustrates the sections 101a, 101b after removal from the patient. Section 101a is referred to as a proximal section and section 101b is referred to as a distal section.

The sections 101a, 101b are required to be removed from the femur 110. The proximal section 101a is exposed above the proximal end of the femur 110 and removed more using various instrumentation. The distal section 101b is recessed within the femur 110 and is generally more difficult to access and remove.

Current methods of removing the distal section include trephine reamers that are inserted over the distal section. The trephine reamers are rotated and have cutting teeth along a distal end that cut the femur to remove the distal section. The teeth are closely spaced together along the distal end. During cutting, the removed bone accumulates in the intermediate space between the teeth. Because of the closeness of the teeth, the intermediate spaces quickly fill with the removed bone and interfere with the teeth thus preventing further bone removal. This requires the surgeon to replace the trephine reamer numerous times during removal of the distal section. During a procedure, a surgeon may be required to use a large number of separate trephine reamers to cut enough bone to remove the femoral component. The process of repeatedly replacing the trephine reamers is burdensome for the surgeon and adds cost to the procedure.

SUMMARY

The patent application is directed trephine reamers and methods of reaming around a stem of a femoral component during removal of the stem. The trephine reamer includes a body with a hollow interior sized to receive the femoral component. A distal end of the body includes one or more teeth shaped for cutting the femur. One or more valleys are positioned between the teeth at the distal end. The one or more valleys accommodate the cut bone and prevent and/or reduce interference with the cutting teeth.

One embodiment is directed to a trephine reamer that includes a body with a distal end, a proximal end, and a hollow interior that extends inward from the distal end. The body includes a longitudinal axis that extends through the distal end and the proximal end and through the hollow interior. Teeth extend axially outward from the distal end along the longitudinal axis. Each of the teeth include a tip, a leading edge extending from the tip along a first side, and a trailing edge extending from the tip along a second side. Valleys are positioned between each of the teeth and are recessed along the longitudinal axis inward from the tips of each of the teeth. Each of the valleys is positioned between a trailing edge of an adjacent first one of the teeth and a leading edge of an adjacent second one of the teeth. Each of the valleys is aligned at a different angular orientation than the trailing edge of the first tooth and the leading edge of the second tooth. Each of the valleys includes a greater width than the adjacent teeth.

Each of the valleys may be flat. Each of the valleys may be aligned in a plane perpendicular to the longitudinal axis.

The teeth may be angled radially inward towards the longitudinal axis.

The leading edge and the trailing edge of each of the teeth may include a common shape and orientation relative to the longitudinal axis.

The teeth may be circumferentially spaced about the distal end of the body and separated by an angle of about 90 degrees.

The trephine reamer may also include a helical groove that extends along the body and includes a first end at the distal end of the body and helically wraps around the body away from the distal end.

Another embodiment is directed to a trephine reamer that includes a cylindrical body with a distal end, a proximal end, and a hollow interior that extends inward from the distal end and is sized to receive the stem of the femoral component. The body also includes a longitudinal axis extending through the body. Teeth are spaced circumferentially around the distal end and extend outward from the distal end. Each of the teeth includes a tip, a leading edge extending from a first side of the tip, and a trailing edge extending from a second side of the tip. Valleys are spaced circumferentially around the distal end and are recessed inward along the longitudinal axis from the tips of the teeth. The valleys are arranged with one of the valleys positioned between each of the teeth. Each of the valleys includes a width measured between the trailing edge and the leading edge of the adjacent teeth. The teeth include a width measured between the leading and trailing edges that is less than the width of the adjacent valleys.

Each of the teeth may include a length measured along the longitudinal axis with the length being between 1.5 to 3.0 times greater than the width.

The teeth may be equally spaced apart about the distal end.

Each of the teeth may be angled inwards towards the longitudinal axis.

The trephine reamer may include a total of two teeth that extend outward from the distal end.

The hollow interior may extend a limited distance inward from the distal end along the longitudinal axis.

Two of the valleys may include different widths.

An angle formed between the trailing edge of each of the teeth and an adjacent valley may be greater than 90°.

The trephine reamer may further include a helical groove that extends along the body with the helical groove including a first end at the distal end of the body and helically wrapping around the body away from the distal end.

Another embodiment is directed to a method of removing a portion of an implanted femoral component from a femur. The method includes inserting a trephine reamer into a femoral canal of the femur. The trephine reamer includes teeth that are spaced apart by valleys with each of the valleys and the teeth including widths measured along the circumference of an outer wall of the trephine reamer with the valleys being wider than the teeth. The method includes positioning the outer wall around the portion of the femoral component that is implanted in the femoral component and positioning the teeth against the femur. The method includes rotating the trephine reamer and moving the teeth against the femur and cutting the femur along the length of the femoral component with the femur being cut along an interior core between an exterior of the femur and the femoral canal. The method also includes accumulating cut portions of the femur within the valleys during rotation of the trephine reamer.

The method may also include: positioning a plunger within an interior of the outer wall and spreading the teeth radially outward; inserting the trephine reamer with the plunger into the femoral canal of the femur; aligning the trephine reamer with the stem; and retracting the plunger from the interior of the outer wall causing the teeth to angle radially inward.

The method may also include rotating the trephine reamer and moving the cut portions of the femur within the valleys away from tips of the teeth.

The method may also include moving the trephine reamer along an exposed portion of the implanted femoral component with the exposed portion being within an interior space formed between the outer wall.

The method may also include simultaneously contacting each of the teeth against the femur during rotation of the trephine reamer.

One embodiment is directed to a trephine reamer for removing a femoral component from a femur. The trephine reamer includes a body with a distal end, a proximal end, and a hollow interior that extends inward from the distal end. The body also includes a longitudinal axis within the hollow interior that extends through the distal end and the proximal section. Teeth are positioned at the distal end with each of the teeth including a tip, a leading edge extending from a first side of the tip, and a trailing edge extending from a second side of the tip. Valleys are positioned at the distal end with each of the valleys positioned between adjacent ones of the teeth and being recessed inward from the tip along the longitudinal axis. The valleys include a greater width than the teeth.

The teeth may include a length that is between 1.5 to 3.0 times their width.

The hollow interior may extend inward from the distal end a limited distance along the longitudinal axis.

The leading edge and the trailing edge may include the same length and the same shape.

The valleys may be substantially flat.

The teeth may be separated by an angle of about 90 degrees.

Another embodiment is directed to a trephine reamer for removing a femoral component from a femur. The trephine reamer includes a body with a distal end, a proximal end, and a hollow interior that extends inward from the distal end. The body includes a longitudinal axis within the hollow interior that extends inward from the distal end. A plurality of teeth extend outward at the distal end with each of the teeth including a tip, a leading edge extending from a first side of the tip, and a trailing edge extending from a second side of the tip. A plurality of valleys are positioned at the distal end with each of the valleys being recessed inward along the longitudinal axis from the tips of the teeth. Each tooth at the distal end is separated from an adjacent tooth by one of the valleys, and the teeth include a width that is less than or equal to a width of the valleys.

The teeth may be positioned around the distal end with the tips of the teeth each being separated by at least a 90° angle of separation.

The teeth may include a length that is between 1.5 to 3.0 times their width.

Each of the teeth may include the same shape.

Each of the teeth may include the same size.

Each of the valleys may be flat.

The teeth may be evenly spaced around the distal end.

There may be a total of two teeth at the distal end.

There may be a total of three teeth at the distal end.

There may be a total of four teeth at the distal end.

Another embodiment is directed to a trephine reamer for removing a femoral component from a femur. The trephine reamer includes a body with a distal end, a proximal end, and a hollow interior that extends inward from the distal end. The body includes a longitudinal axis within the hollow interior that extends through the distal end. A plurality of teeth extend outward at the distal end with each of the teeth including a tip. A plurality of valleys are positioned at the distal end with each of the valleys being recessed inward along the longitudinal axis from the tips of the teeth. One of the valleys is positioned between each of the teeth with valleys including a greater width than the teeth.

The teeth may be equally spaced apart about the distal end.

Each of the valleys may be sized to space the teeth apart by at least a 90° angle of separation.

Another embodiment is directed to a method of removing a portion of a femoral component from a femur of a patient. The method includes inserting a trephine reamer into a femoral canal of the patient, the trephine reamer including a distal end with a plurality of teeth that are spaced apart by valleys with the valleys including a greater width than the teeth. The method includes rotating the trephine reamer and moving the trephine reamer along the femur while cutting the femur along an exterior of the femoral component. The distal end of the trephine reamer being shaped with the cut bone moving into valleys between the teeth during rotation of the trephine reamer.

The various aspects of the various embodiments may be used alone or in any combination, as is desired.

DETAILED DESCRIPTION

The present application discloses trephine reamers and methods of cutting bone during removal of a femoral component of a hip prosthesis. The trephine reamers are applicable for reaming around the stem of a femoral implant, and are particularly applicable for use with broken stems. The trephine reamer includes a body with a hollow interior sized to receive the femoral component. A distal end of the body includes one or more teeth shaped for cutting the femur. Valleys are positioned between the teeth. The valleys accommodate the cut bone and prevent and/or reduce interference with the cutting teeth. Thus, a single trephine reamer is able to cut a greater amount of bone.

Figure 3:
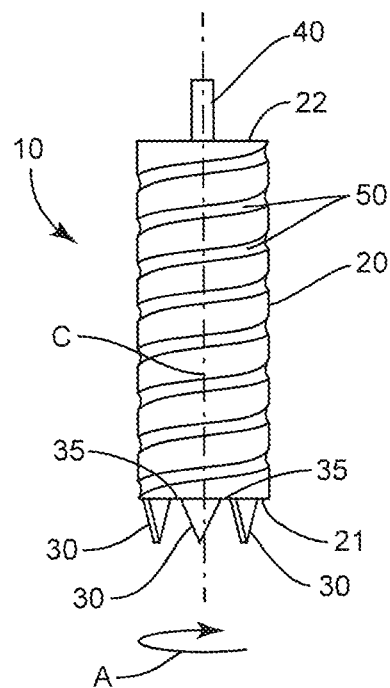
FIG. 3 is a side view of a trephine reamer.

FIG. 3 illustrates a trephine reamer 10 used for cutting bone during removal of a femoral component. The trephine reamer 10 includes a body 20 with a distal end 21 and an opposing proximal end 22. This embodiment includes three teeth 30 that each extend axially outward beyond the distal end 21 and are configured to cut bone. Valleys 35 are located at the distal end 21 between each of the teeth 30. The teeth 30 each extend axially outward beyond the valleys 35. The teeth 30 are positioned to contact and cut the bone during rotation of the trephine reamer 10. The cut bone accumulates in the valleys 35 which are axially below the tip of each tooth 30. This provides for the teeth 30 to remain better exposed during the cutting procedure such that the trephine reamer 10 can be used to cut a greater amount of bone than previous devices.

The trephine reamer 10 also includes a mount 40 positioned at the proximal end 22. The mount 40 provides for applying a torque to the trephine reamer 10 for rotation in the direction of arrow A about a longitudinal axis C. The mount 40 may be configured for attachment to a powered device that applies rotation to the trephine reamer 10. Mount 40 may also be configured to receive a manual rotational force. In one embodiment, the mount 40 includes a handle for the surgeon to manually apply a rotational force.

Figure 4:
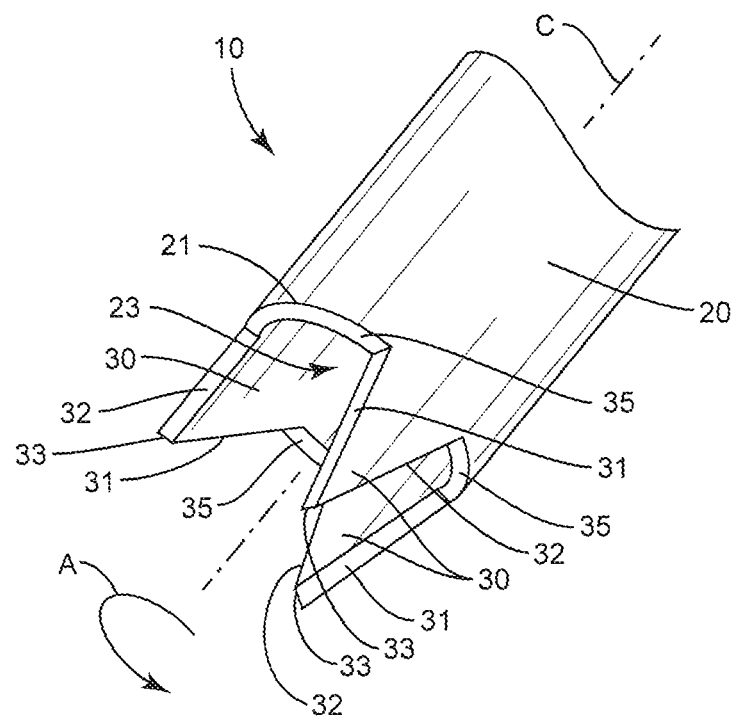
FIG. 4 is a perspective view of a distal end of a trephine reamer.

FIG. 4 illustrates a distal end 21 of a trephine reamer 10 that includes three teeth 30. Each of the teeth 30 is configured to cut bone when the trephine reamer 10 is rotated in the direction indicated by arrow A. Each tooth 30 includes a tip 33, a leading edge 31 and a trailing edge 32. The leading and trailing edges 31, 32 taper from the tip 33 to an adjacent valley 35. The valleys 35 are positioned adjacent to the teeth 30 and are axially recessed along the longitudinal axis C inward from the tips 33. The valleys 35 provide space to receive the cut bone such that the teeth 30 remain exposed to further cut the bone.

Figure 5:
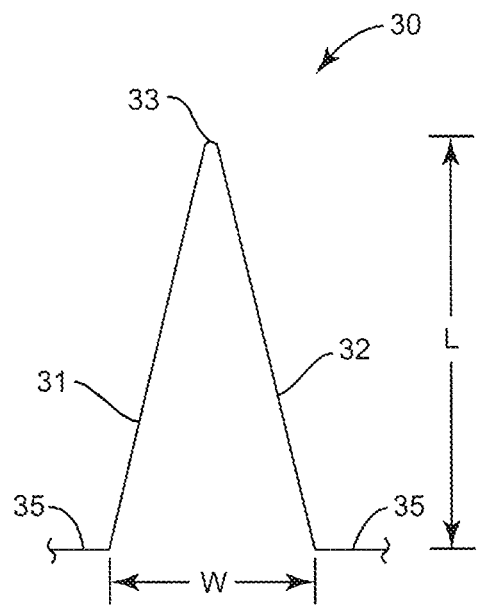
FIG. 5 is a schematic side view of a tooth and adjacent valleys of a trephine reamer.

FIG. 5 illustrates a side view of a tooth 30 positioned between adjacent valleys 35. The tooth 30 includes a leading edge 31, a trailing edge 32, and a tip 33. The tooth 30 is symmetrical with the edges 31, 32 having the same size and angular positioning. Trephine reamers 10 may also include other teeth 30 with a variety of different edges 31, 32 with various shapes and/or sizes and/or angular orientations.

The tooth 30 includes a width W measured between outer points of the leading and trailing edges 31, 32. The tooth 30 also includes a length L measured between the tip 33 and valleys 35. Preferably, the teeth 30 include a length L that is 1.5 to 3.0 times the width W. In one specific embodiment, the teeth 30 include a length L that is twice the width (i.e., the length L is 2.0 times the width W). Other embodiments include teeth 30 with various lengths L and widths W.

Figure 6:
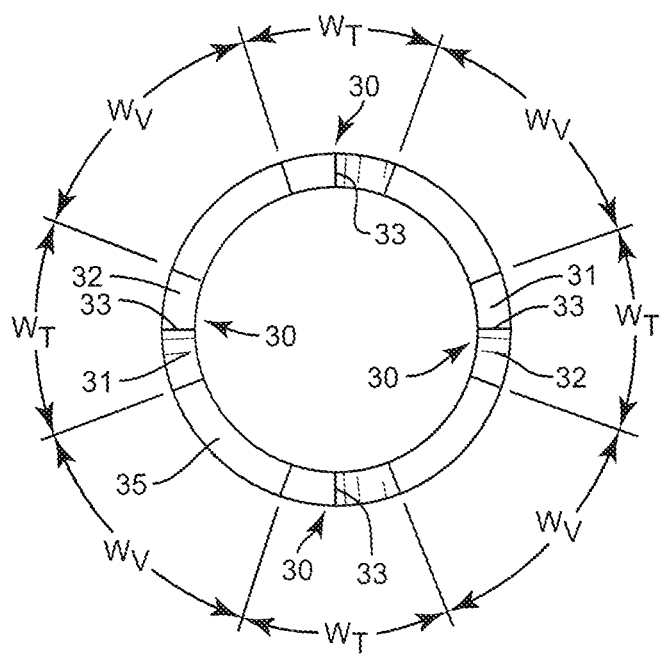
FIG. 6 is a schematic view of a distal end of a trephine reaming illustrating the widths of teeth and valleys of a trephine reamer.

FIG. 6 illustrates an end view of a trephine reamer 10 that includes four teeth 30 that are spaced around the distal end. Each tooth 30 includes a tip 33 that is formed between a leading edge 31 and a trailing edge 32. Each of the teeth 30 includes a width $W_T$ measured around the distal end 21 of the body 20. Likewise, each of the valleys 35 includes a width $W_V$. Preferably, the widths of the valleys $W_V$ are greater than or equal to the widths of the teeth $W_T$. This spacing provides for the cut bone to accumulate in the valleys 35 and prevent or reduce interference with the teeth 30 during the cutting process.

Figure 8:
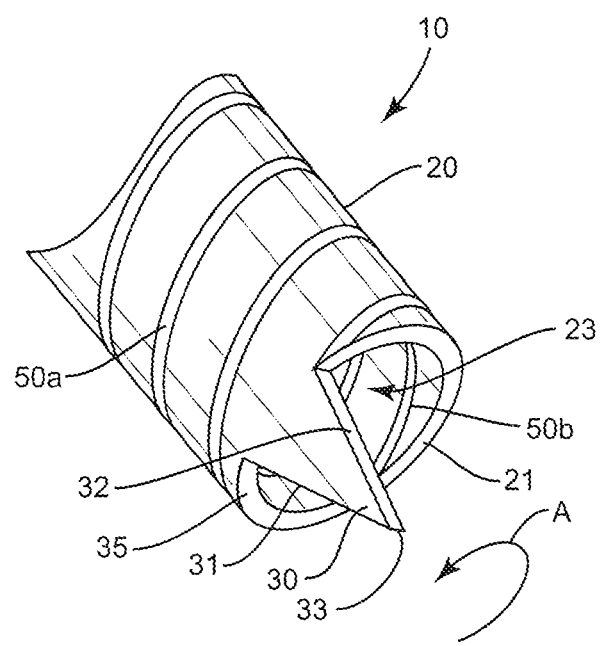
FIG. 8 is a perspective view of a distal end of a trephine reamer with a single tooth.

The number of teeth 30 positioned at the distal end 21 may vary, provided that the arrangement includes adequate valley space to accommodate the cut bone. Preferably, the distal end 21 includes between two and four teeth 30. This provides for distributing the cutting along the distal end 21 and still provides for adequate space to receive the cut bone. In one embodiment as illustrated in FIG. 8, the trephine reamer 10 includes a single tooth 30 positioned at the distal end 23.

Figure 7:
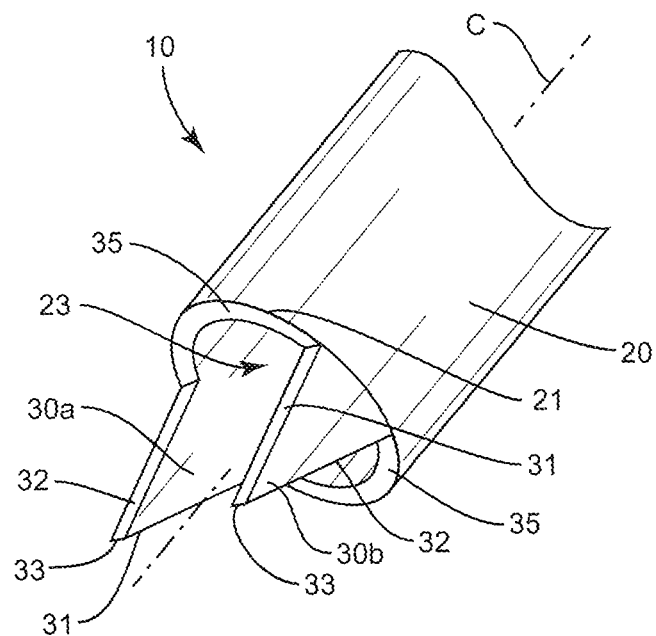
FIG. 7 is a perspective view of a distal end of a trephine reamer with teeth and valleys.
Figure 7A:
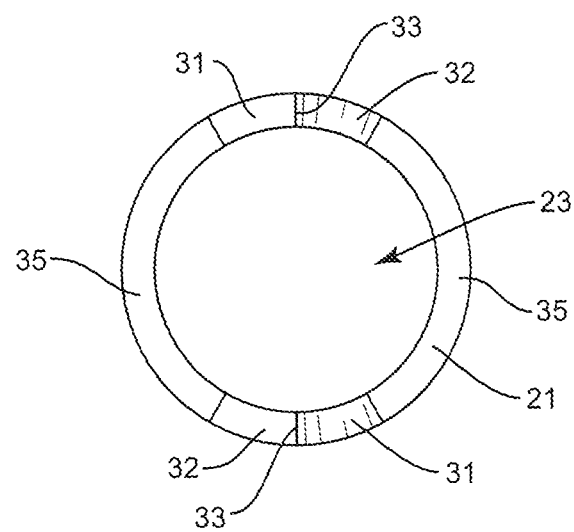
FIG. 7A is an end view of the distal end of the trephine reamer of FIG. 7.

FIG. 7 includes an embodiment with two teeth 30 positioned at the distal end 21. Each tooth 30a, 30b includes a tip 33, a leading edge 31, and a trailing edge 32. This design further includes valleys 35 positioned between each of the teeth 30. FIG. 7A illustrates an end view of the distal end 21 of the trephine reamer 10 of FIG. 7. The teeth 30 are positioned on opposing sides of the hollow interior 23.

Figure 9:
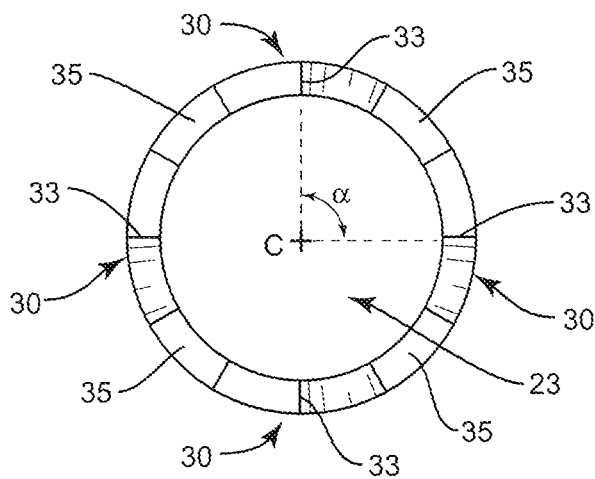
FIG. 9 is a schematic view of a distal end of a trephine reamer.

The relative sizing of the widths of the teeth 30 and valleys 35 also provides for angular spacing between the teeth 30. FIG. 9 illustrates an embodiment with four teeth 30 spaced about the distal end 21. An angle α is formed at the longitudinal axis C between the tips 33 of adjacent teeth 30. In one embodiment, the minimum angle α between adjacent teeth 35 is 90°. This ensures the valleys 35 include adequate space to receive the cut bone and prevent interference with the teeth 30. This required spacing also results in a design with a maximum of four teeth 30 at the distal end 21. The angle α between teeth 35 will vary depending upon the configuration of the teeth 35 at the distal end 21. By way of example, the teeth 30 of trephine reamer 10 of FIGS. 7 and 7A are spaced apart by an angle of about 180°.

Figure 10:
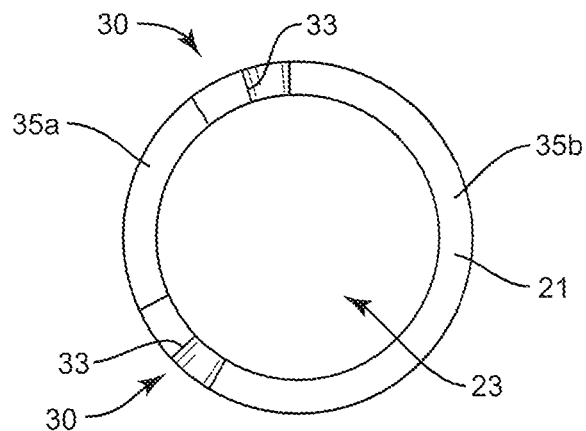
FIG. 10 is a schematic view of a distal end of a trephine reamer.

In embodiments with multiple teeth 30, the teeth 30 may be equally spaced apart about the distal end 21. Other embodiments may include different spacing between the teeth 30. In the unequal spacing embodiments, the teeth 30 may be positioned at various locations provided that the width of the valleys 35 is greater than or equal to the widths of the teeth 30. FIG. 10 illustrates an embodiment with unequal teeth spacing between the two teeth 30. The teeth 30 are positioned with a first valley 35*a* being substantially smaller than a second valley 35*b*. The width of the first valley 35*a* is greater than or equal to the width of the teeth 35.

Figure 11:
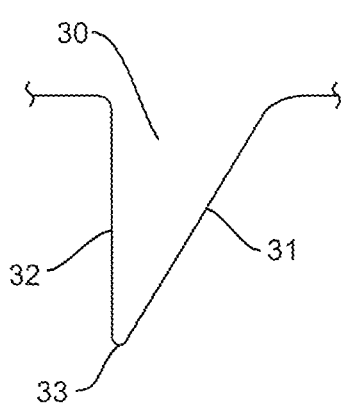
FIG. 11 is a schematic side view of a tooth and adjacent valleys of a trephine reamer.

The teeth 30 are configured to cut the femur 110 when the trephine reamer 10 is rotated about the longitudinal axis C. The shape of the teeth 30 may vary. In one embodiment as illustrated in FIG. 5, the tooth 30 is symmetrical with the leading edge 31 and the trailing edge 32 including the same shape and length. Other embodiments may include different shapes. FIG. 11 includes an embodiment of a tooth 30 with a non-symmetrical shape and the edges 31, 32 being of different lengths. In embodiments with multiple teeth 30, the teeth 30 may include the same or different shapes and/or sizes. In embodiments with multiple teeth 30, it is preferred that each tooth 30 includes the same length such that each cuts the bone and the trephine reamer 10 tracks along the femoral component 101 during the cutting process.

The one or more valleys 35 may also vary in shape depending upon the embodiment. In one embodiment as illustrated in FIG. 7, the valleys 35 are relatively flat and lie within a common plane axially positioned below the tooth tips 33. Other embodiments may include the valleys 35 having other different axial depths below the level of the tips 33. In embodiments with multiple valleys 35, each may include different shapes.

The body 20 of the trephine reamer 10 includes a cylindrical shape with a hollow interior 23. The interior 23 is sized to receive the portion of the femoral component that remains within the femur 110. The hollow interior 23 may extend along the entirety of the body 20, or may extend inward from the distal end 21 a limited distance along the length of the body 20. The body 20 may include an interior diameter that is constant along the length. Other embodiments may include an interior diameter that varies along the length. The body 20 may be constructed of various materials, including various metals such as but not limited to stainless steel.

As illustrated in FIGS. 3 and 8, one or more helical grooves 50 may extend along the body 20. The grooves 50 may extend along the exterior surface of the body 20 and/or along the interior surface at the hollow interior 23. FIG. 8 illustrates a first groove 50*a* extending along the exterior and a second groove 50*b* extending along the interior. The grooves 50 may extend along the entire length of the body 20, or along one or more limited sections. In one embodiment, the grooves 50 start at the distal end 21. The grooves 50 receive the cut bone and move it towards the proximal end 22. The grooves 50 further facilitate removal of the bone from the cutting site and prevent the cut bone from interfering with the one or more teeth 30.

The surgical phase of using the trephine reamer 10 to remove a distal portion 101*b* or stem of a femoral component includes placing the patient in a position to provide access to the femur 110. Once positioned, an incision is made to expose the proximal end of the femur 110 and the portion of the proximal femoral section 101*a* that extends outward from the femur 110.

The proximal section 101*a* of the femoral component 101 is initially removed from the femur 110. This may include using a variety of different instruments/devices. Once removed, the distal section 101*b* is accessible within the femoral canal.

A trephine reamer 10 of appropriate size is selected for insertion into the femur 110 to remove the distal portion. The size may be determined based on various factors, including the size of the distal portion remaining in the femur 110 and the amount of bone growth between the component 101 and the femur 110. The size is selected with the hollow interior 23 sized to extend over and receive the component 101*b*. Preferably, the trephine reamer 10 is sized with an inner diameter of the interior 23 closely matching the distal portion to prevent removal of an excessive amount of bone.

The surgeon positions the distal end 21 of the trephine reamer 10 with the distal portion of the femoral component 101*b*. The distal end 21 is aligned, and the trephine reamer 10 is then rotated around the component 101 by either a power tool attached to the mount 40 or manually by the surgeon. The surgeon may further apply a force to the trephine reamer 10 to move the trephine reamer 10 along the length of the component 101*b* during the cutting process.

The teeth 30 on the distal end 21 contact against and cut the bone during rotation of the trephine reamer 10. The cut bone is then moved into the adjacent one or more valleys 35 and away from the teeth 30. This provides for the teeth 30 to remain exposed for further contact and cutting of the bone. Additional bone may be removed from the cutting site from the one or more grooves 50 that extend along the trephine reamer 10.

The surgeon may provide a constant force to move the trephine reamer 10 through the bone and along the distal portion. Alternatively, the surgeon may periodically pull the trephine reamer 10 backwards in an opposing direction. This back-and-forth cutting style may facilitate moving the cut bone away from the one or more teeth 30 and into the one or more valleys 35.

Once the cutting is complete, the surgeon removes the trephine reamer 10 from the femoral canal. Additional devices may then be inserted to access and remove the component 101*b*. The depth of the cutting along the femur 110 may vary depending upon the circumstances. In some embodiments, the femur 110 is cut through to the distal end of the component 101*b*. Other embodiments include the cutting stopping before reaching the distal end.

Once the cutting is complete, the surgeon removes the trephine reamer 10 from the femur 110. The component 101*b* is then able to be removed from the femur 110.

Figure 1:
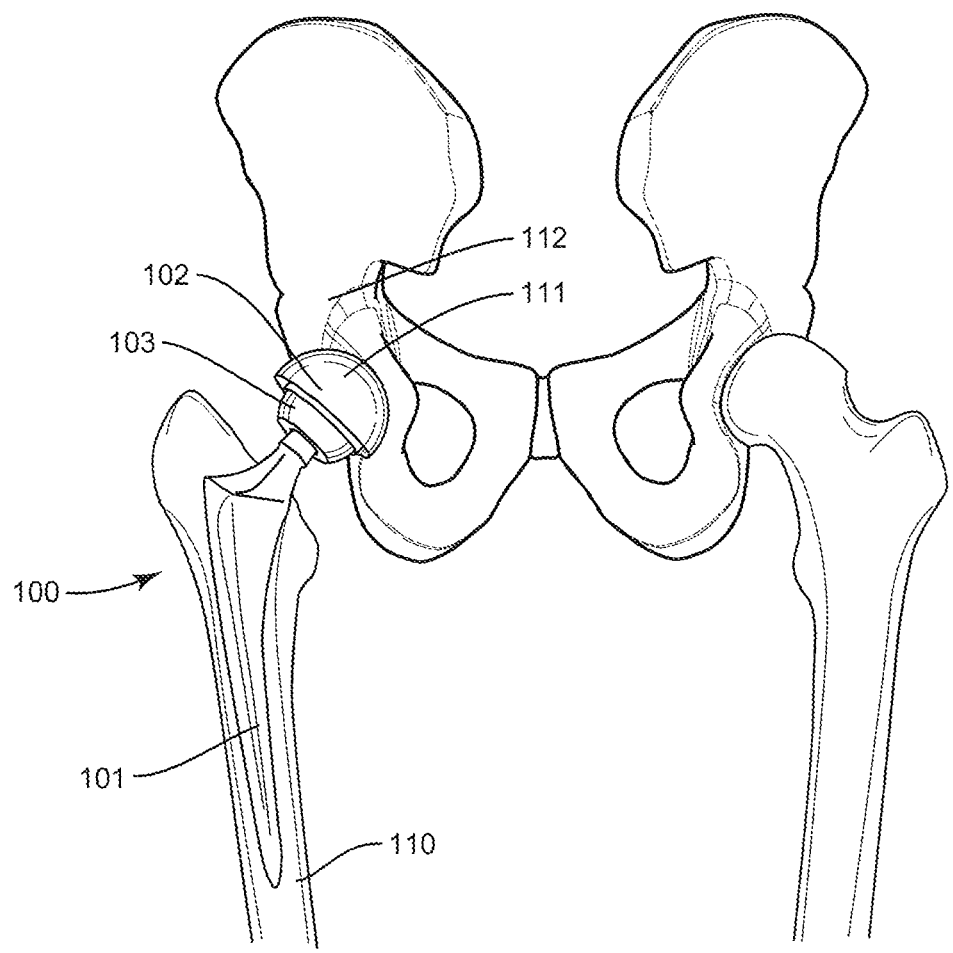
FIG. 1 is a side schematic view of a hip replacement implant mounted within a patient.
Figure 2A:
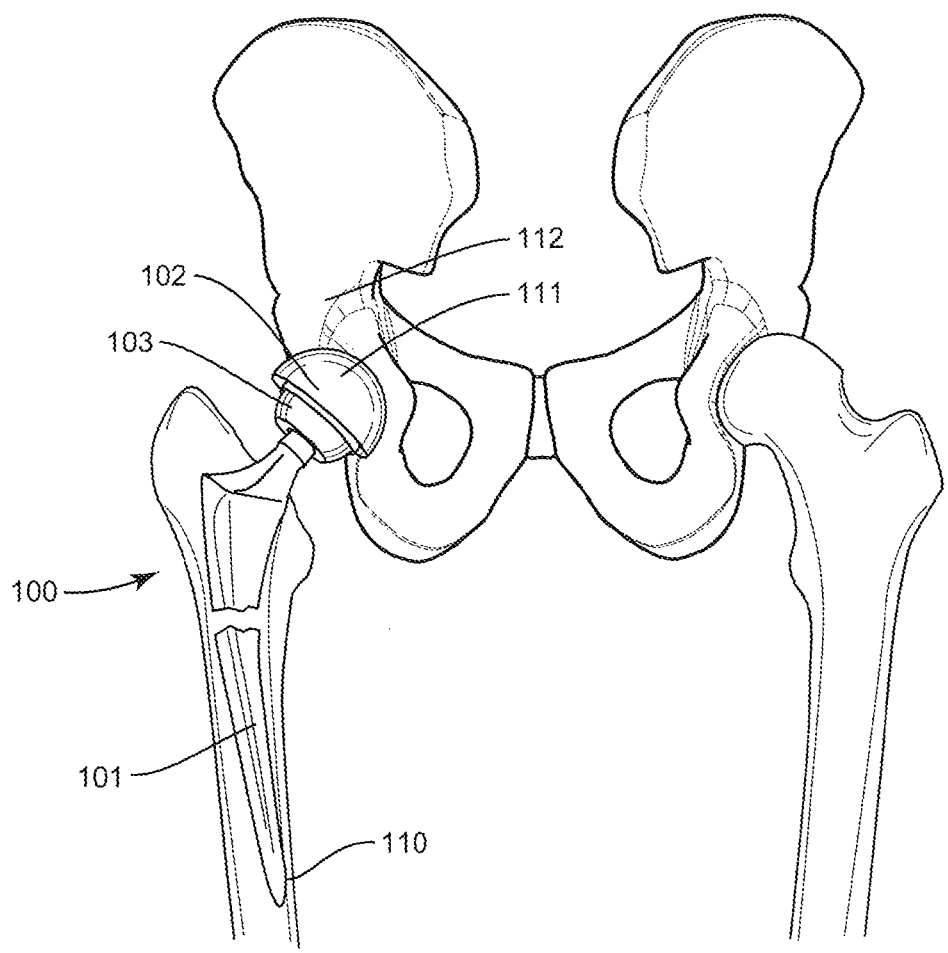
FIG. 2A is a schematic view of broken femoral component of a hip prosthesis within a patient's femur.
Figure 2B:
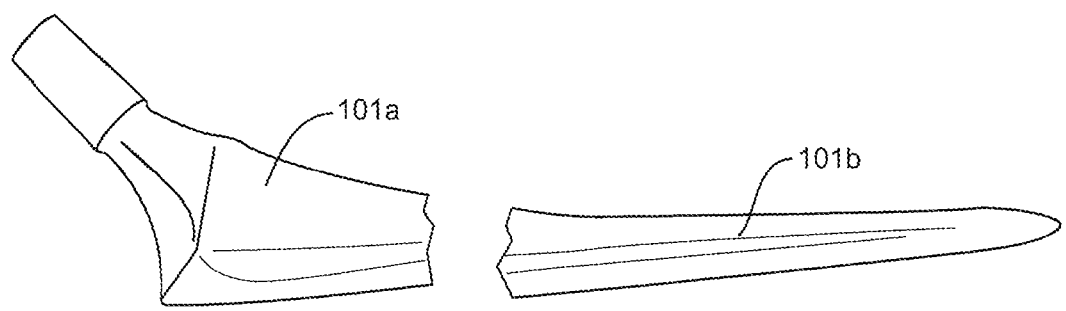
FIG. 2B is a side view of a broken femoral component.

The trephine reamer 10 may be used primarily in two situations. A first situation includes a femoral component 101 with a broken stem as illustrated in FIGS. 2A and 2B. A second situation includes a disassembled modular stem. In both situations, the trephine reamer 10 is used to remove the distal section of the implant.

Figure 12:
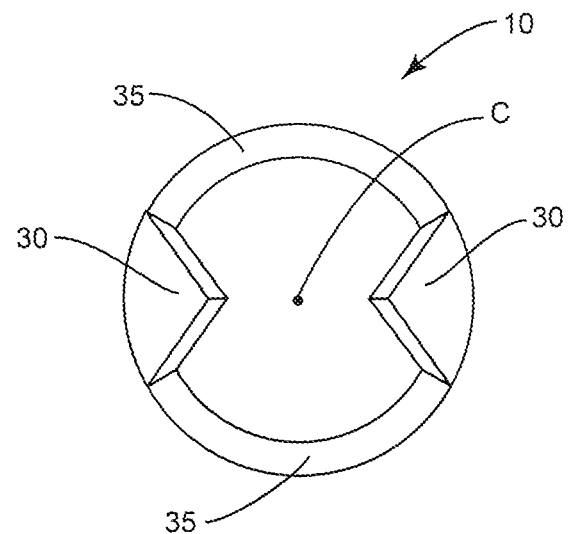
FIG. 12 is an end view of the distal end of the trephine reamer with teeth angled radially inward.

In one or more embodiments, the teeth 30 extend directly outward from the distal end 21 of the body 20. As illustrated in FIGS. 6, 7A, and 9, the teeth 30 are aligned with the body 20 when viewed from the end of the trephine reamer 10. In one or more embodiments, the teeth 30 are angled radially inward towards a center of the hollow interior 23. FIG. 12 illustrates one embodiment with each of the two teeth 30 angled radially inward towards the longitudinal axis C. The extent of the angle may vary depending upon the context. In one specific embodiment, the teeth 30 include a slight radial inward bend.

Figure 13:
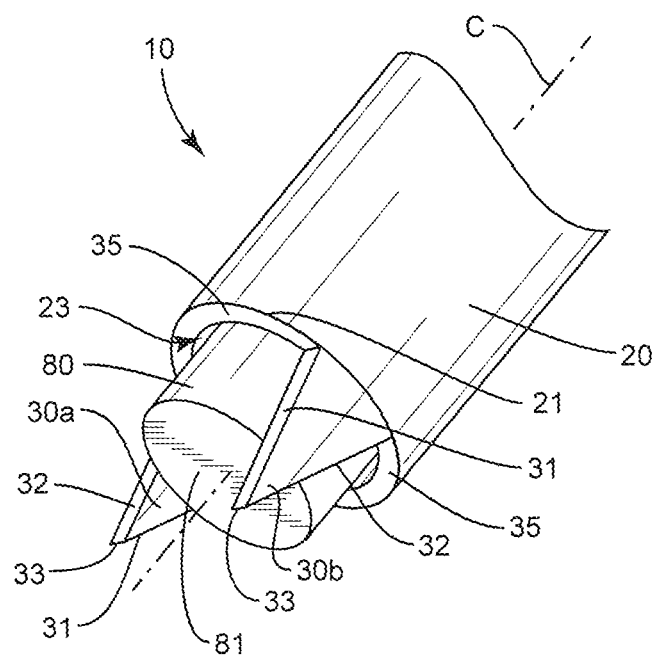
FIG. 13 is a perspective view of the distal end of the trephine reamer of FIG. 12 with a plunger inserted within the hollow interior.

Trephine reamers 10 with inwardly-angled teeth 30 may be used in combination with a plunger 80 as illustrated in FIG. 13. The plunger 80 is sized to fit within the interior space 23 of the trephine reamer 10. The plunger 80 includes a distal end 81 that contacts against an inner side of the teeth 30 and spreads them outward away from the longitudinal axis C.

In use as illustrated in FIG. 13, the plunger 80 is inserted through the middle of the trephine reamer 10 including the hollow interior 23. The distal end 81 of the plunger 80 contacts against the inner side of the teeth 30 and spreads the teeth 30 radially outward away from the hollow interior 23. In one or more embodiments, the plunger 80 is sized to closely approximate the size and shape of the interior space 23 such that the plunger 80 spreads the teeth 30 to be aligned with the body 20 when viewed from the end of the trephine reamer 10.

During use, the trephine reamer 10 with the inserted plunger 80 are both inserted into the patient. The trephine reamer 10 is positioned at the implanted stem 101b with the teeth 30 being spread outward by the plunger 80. Once the trephine reamer 80 is positioned relative to the stem 101b, the plunger 80 is retracted causing the teeth 30 to flex inward against the stem 101b (not illustrated in FIG. 13). The trephine reamer 10 is then rotated as described above. During the rotation, the teeth 30 are angled inward toward the stem during the reaming process. A trephine reamer 10 with inwardly-angled teeth 30 may be particularly helpful for removing femoral components with tapered stems. The teeth 30 remain against and/or in proximity to the stem during the reaming down along the length of the stem towards its distal end.

The various implants and insertion tools may be used during surgical procedures on living patients. These may also be used in a non-living situation, such as within a cadaver, model, and the like. The non-living situation may be for one or more of testing, training, and demonstration purposes.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc. and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

The invention claimed is:

1. A trephine reamer for reaming around a stem of a femoral component implanted in a femur, the trephine reamer comprising:
   a cylindrical body with a distal end, a proximal end, and a hollow interior that extends inward from the distal end, the hollow interior sized to receive the stem of the femoral component, the body including a longitudinal axis that extends through the hollow interior and the distal end and the proximal end;
   only one, two, or three teeth extending directly axially outward from the distal end along the longitudinal axis and being aligned with the body when viewed along the longitudinal axis, the teeth being spaced apart to form a gap between interiors of the teeth that is sized to receive the stem of the femoral component, each of the teeth including a tip, a leading edge extending from the tip along a first side, and a trailing edge extending from the tip along a second side, each of the teeth including a width measured between the leading and trailing edge;
   valleys positioned between each of the teeth and being recessed along the longitudinal axis inward from the tips of each of the teeth, each of the valleys being positioned between a trailing edge of an adjacent first one of the teeth and a leading edge of an adjacent second one of the teeth, each of the valleys being aligned at a different angular orientation than the trailing edge of the first tooth and the leading edge of the second tooth, each of the valleys including a width measured between the trailing edge of the first one of the teeth and the leading edge of the second one of the teeth; each of the valleys including a greater width than the adjacent teeth.

2. The trephine reamer of claim 1, wherein each of the valleys is flat.

3. The trephine reamer of claim 1, wherein each of the valleys is aligned in a plane perpendicular to the longitudinal axis.

4. The trephine reamer of claim 1, wherein the leading edge and the trailing edge of each of the teeth include a common shape and orientation relative to the longitudinal axis.

5. The trephine reamer of claim 1, wherein the teeth are circumferentially spaced about the distal end of the body and separated by an angle of about 90 degrees.

6. The trephine reamer of claim 1, further comprising a helical groove that extends along the body, the helical groove including a first end at the distal end of the body and helically wrapping around the body away from the distal end.

7. The trephine reamer of claim 1, wherein the body is constructed from stainless steel.

8. A trephine reamer for reaming around a stem of a femoral component implanted in a femur, the trephine reamer comprising:
   a cylindrical body with a distal end, a proximal end, and a hollow interior that extends inward from the distal end and is sized to receive the stem of the femoral component, the body including a longitudinal axis:
   only one, two, or three teeth spaced circumferentially around the distal end and that extend directly outward from the distal end and are aligned with the body and with a gap formed between interiors of the teeth that is aligned on the longitudinal axis and sized to receive the stem of the femoral component, each of the teeth including a tip, a leading edge extending from a first side of the tip, and a trailing edge extending from a second side of the tip;

valleys spaced circumferentially around the distal end and being recessed inward along the longitudinal axis from the tips of the teeth, the valleys being arranged with one of the valleys positioned between each of the teeth, each of the valleys including a width measured between the trailing edge and the leading edge of the adjacent teeth;

the teeth including a width measured between the leading and trailing edges that is less than the width of the adjacent valleys.

9. The trephine reamer of claim 8, wherein each of the teeth includes a length measured along the longitudinal axis, each of the teeth including the length being between 1.5 to 3.0 times greater than the width.

10. The trephine reamer of claim 8, wherein the teeth are equally spaced apart about the distal end.

11. The trephine reamer of claim 8, wherein the hollow interior extends a limited distance inward from the distal end along the longitudinal axis.

12. The trephine reamer of claim 8, wherein two of the valleys include different widths.

13. The trephine reamer of claim 8, wherein an angle formed between the trailing edge of each of the teeth and an adjacent valley is greater than 90°.

14. The trephine reamer of claim 8, further comprising a helical groove that extends along the body, the helical groove including a first end at the distal end of the body and helically wrapping around the body away from the distal end.

* * * * *